United States Patent [19]

Bednarski et al.

[11] 4,121,034

[45] Oct. 17, 1978

[54] BIOLOGICALLY ACTIVE TRIORGANOTIN COPOLYMERS

[75] Inventors: John R. Bednarski, Flushing, N.Y.; David B. Russell, Westfield, N.J.

[73] Assignee: M&T Chemicals Inc., Stamford, Conn.

[21] Appl. No.: 805,838

[22] Filed: Jun. 13, 1977

Related U.S. Application Data

[62] Division of Ser. No. 738,001, Nov. 2, 1976.

[51] Int. Cl.$^2$ .................... C08F 30/04; C08F 130/04; C08F 230/04; C08F 4/32

[52] U.S. Cl. .................................... 526/240; 47/58; 71/67; 260/33.6 UA; 424/78; 424/81; 424/288; 526/232.1

[58] Field of Search .................... 526/240; 424/78, 81, 424/288

[56] References Cited

U.S. PATENT DOCUMENTS

| | | | |
|---|---|---|---|
| 3,016,369 | 1/1962 | Montermoso et al. | 526/240 |
| 3,167,473 | 1/1965 | Leebrick | 526/240 |
| 3,167,532 | 1/1965 | Leebrick | 526/240 |
| 3,423,482 | 1/1969 | Katsumura et al. | 526/240 |
| 3,426,002 | 2/1909 | Frankel et al. | 526/240 |
| 3,555,148 | 1/1971 | Katsumura et al. | 576/240 |
| 3,804,816 | 4/1974 | Samoilov et al. | 526/240 |
| 3,979,354 | 9/1976 | Dyckman et al. | 526/240 |

FOREIGN PATENT DOCUMENTS

| | | | |
|---|---|---|---|
| 4,323,867 | 10/1968 | Japan | 526/240 |
| 255,564 | 4/1970 | U.S.S.R. | 526/240 |
| 1,270,922 | 4/1972 | United Kingdom | 526/240. |

*Primary Examiner*—Herbert J. Lilling
*Attorney, Agent, or Firm*—Kenneth G. Wheeless; Robert Spector

[57] ABSTRACT

The undesirable swelling exhibited by biologically active copolymers wherein a portion of the repeating units exhibit a triorganotin moiety ($R_3SN$—) is reduced by incorporation of a cross-linking agent into the copolymer. The physical and chemical properties of the cross-linked copolymers make them more suitable for use as biocides particularly antifouling toxicants, than polymers described in the prior art.

14 Claims, No Drawings

BIOLOGICALLY ACTIVE TRIORGANOTIN COPOLYMERS

This is a divisional of application Ser. No. 738,001, filed Nov. 2, 1976.

BACKGROUND OF THE INVENTION

This invention relates to novel copolymers incorporating a triorganotin moiety. This invention further relates to tin-containing polymers which retain efficacious levels of biological activity over a longer period of time relative to prior art materials.

The biological activity of polymers containing at least one triorganotin moiety ($R_3Sn-$) is well known. U.S. Pat. No. 3,167,473 discloses polymers obtained by polymerizing triorganotin derivatives of ethylenically unsaturated acids, including acrylic, methacrylic, and vinyl-benzoic acids. The resultant products are employed as the toxicant in antifouling marine coatings and in compositions applied to agricultural food crops for the purposes of protecting them against infestation by a variety of harmful organisms, particularly fungi.

It has now been found that the biological activity of a given organotin-containing polymer, particularly when exposed to water, is strongly influenced by the extent to which the polymer swells as the triorganotin radicals ($R_3Sn-$) are gradually removed by hydrolysis. Specifically, superior results are obtained if the copolymer incorporates a moiety with a functionality of 3 or more, such as a residue derived from 1,3-butane diol glycol dimethacrylate, ethylene glycol dimethacrylate, or divinyl benzene.

SUMMARY OF THE INVENTION

This invention provides novel biologically active copolymers obtained by reacting at least one solubilized triorganotin compound of the general formula

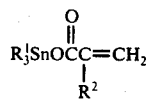

with at least one solubilized copolymerizable monomer of the general formula

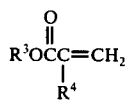

and from 0.01 to 10%, based on total monomer weight, of a solubilized crosslinking agent. The triorganotin compound constitutes from 30 to 70 mole % of the total monomers.

DETAILED DESCRIPTION OF THE INVENTION

The present crosslinked copolymers are prepared using conventional methods of solution polymerization in the presence of an inert liquid medium that preferably consists essentially of at least one liquid aliphatic or cycloaliphatic hydrocarbon containing from 5 to 16 carbon atoms. Optionally the liquid medium may contain up to 50% by volume of at least one liquid aromatic hydrocarbon. In the foregoing formulae each of the three $R^1$ represents an alkyl radical containing from 1 to 8 carbon atoms, a cycloalkyl or an aryl radical. The three $R^1$ radicals may be the same or different. Methods for preparing asymmetric triorganotin compounds are well known. A preferred method is disclosed in U.S. Pat. No. 3,789,057, the pertinent portions of which are hereby incorporated by reference. $R^2$ and $R^4$ are individually selected from the group consisting of hydrogen and methyl and $R^3$ represents an alkyl radical containing from 1 to 18 carbon atoms, a cycloalkyl or a phenyl radical.

The triorganotin compounds employed to prepare the biologically active polymers are derivatives of acrylic or methacrylic acid. The compounds are conveniently obtained by reacting the acid or other suitable derivative such as an ester or halide with the desired triorganotin oxide, hydroxide or halide. If a halide is used, the reaction is conventionally carried out in the presence of a suitable acid acceptor as is well known in the art.

Preferred triorganotin compounds contain a total of from 3 to 24 carbon atoms bonded to the tin atom. Representative compounds of this type are trimethyltin methacrylate, tri-n-butyltin acrylate, tri-n-propyltin methacrylate, trioctyl-, tricyclohexyl- and triphenyltin acrylates and triphenyltin methacrylate. One or more of these compounds is reacted with the crosslinking agent and at least one copolymerizable monomer that is preferably selected from the group consisting of esters of acrylic and methacrylic acids. Vinyl monomers such as vinyl chloride, styrene, vinyl acetate and vinyl butyrate are also useful, as are maleic acid, acrylic acid, methacrylic acid, acrylamide and acrylonitrile.

Any of the crosslinking agents conventionally used for acrylic ester polymers can be employed to reduce swelling and increase the useful life of the present biologically active polymers. Preferred crosslinking agents include divinyl benzene and esters derived from acrylic or methacrylic acid and glycols or polyols containing two, three or four hydroxyl groups. Suitable glycols include ethylene glycol, 1,2-propanediol, 1,3-propanediol, 1,2-butane diol, 1,4-butanediol and 1,4-cyclohexanediol. Useful trifunctional alcohols include glycerol and trimethylolpropane. Pentaerythritol is an example of a tetrafunctional alcohol. Polyfunctional phenols such as pyrocatechol, resorcinol and Bisphenol A (4,4'-iso-propylidenediphenol) are also suitable reactants for preparing the present crosslinking agents. The crosslinking agents contain at least two polymerizable double bonds located between adjacent carbon atoms. Specific examples of useful crosslinking agents are:

1,3-Butanediol Dimethacrylate
Ethylene Glycol Diacrylate
Ethylene Glycol Dimethacrylate
Bisphenol A Dimethacrylate
Diethylene Glycol Dimethacrylate
Pentaerythritol Triacrylate
Pentaerythritol Tetraacrylate
Triethylene Glycol Dimethacrylate
Trimethylolpropane Trimethacrylate
Tetraethylene Glycol Dimethacrylate
Trimethylolpropane Triacrylate
Tetraethylene Glycol Diacrylate
Ethoxylated Bisphenol A Dimethacrylate
Pentaerythritol Tetramethacrylate Additionally, one can also employ organotin compounds containing 2 or 3 acrylic or methacrylic acid residues. These compounds are diorganotin diacrylates or -dimethacrylate and monoorganotin triacrylates and -trimethacrylates. Preferably the hydrocarbon radicals bonded to the tin atom are selected from the same group as $R^1$ in the preceding formula.

The concentration of crosslinking agent is preferably from 0.1 to 5%, based on total monomer weight.

The polymer is prepared by dissolving the desired monomer mixture, including the crosslinking agent, in a suitable liquid hydrocarbon medium, as specified hereinbefore, which contains a free radical initiator. The polymerization can be carried out at any conventional temperature, however temperatures in the range from 40° to 90° C. are preferred. The free radical initiator should be soluble in the polymerization medium and exhibit a half life of from 20 min. to 120 hours at the polymerization temperature. Suitable initiators include the conventional peroxides and hydroperoxides such as benzoyl peroxide and cumene hydroperoxide. The concentration of initiator is conventionally from about 0.001 to 0.01 mole %, based on total monomers. The total concentration of monomers should be from 1.5 to 10 moles per liter of reaction mixture, preferably from 2 to 5 moles per liter, to obtain a conversion to polymer of 95% or higher.

Liquid hydrocarbons that constitute the preferred media for preparing the present copolymers include pentane, hexane, heptane, octane, cyclohexane and cyclooctane. Mixtures containing two or more of these hydrocarbons are also suitable. Such mixtures are commercially available as petroleum ether, mineral spirits, ligroin and Varsol ® (a registered trademark of the Exxon Company). The polymerization medium should be a solvent for all of the monomers, the final polymer and the free radical initiator.

The physical and chemical properties of crosslinked polymers prepared in accordance with the present method using liquid aliphatic or cycloaliphatic hydrocarbons containing from 5 to 16 carbon atoms differ considerably from organotin-containing polymers disclosed in the prior art. The latter class of polymers are obtained by bulk, aqueous emulsion or solution polymerization in the absence of a crosslinking agent. Bulk and emulsion polymerization are exemplified in the aforementioned U.S. Pat. No. 3,167,473. The extent to which the present crosslinked polymers swell in aqueous media is lower than polymers disclosed in said patent. Additionally, the rate at which the tin-containing species is released from the polymer by hydrolysis is considerably slower, yet is sufficient to achieve the desired level of biological activity. The crosslinked polymers will therefore retain their biological activity over a longer period of time relative to polymers prepared using other conventional techniques. This is particularly advantageous when the polymer is incorporated as the active toxicant in an antifouling coating formulation, since the ship or other structure will require less frequent repainting.

It is well known that the difference in physical properties and chemical reactivity exhibited by polymers of the same monomer composition are indicative of structural differences, particularly the order in which the repeating units are arranged along the polymer molecule. Polymers prepared using aliphatic or cycloaliphatic liquid hydrocarbons containing from 5 to about 16 carbon atoms are particularly preferred, since it is believed that polymers prepared in this manner exhibit an alternating arrangement of repeating unit. This can be accounted for by formation of a complex between the triorganotin compound and the other comonomers.

The presence of aromatic solvents such as xylene inhibits complex formation between the comonomers resulting in a more random distribution of repeating units. The degree of alternation is, of course, also dependent upon the relative concentrations of the various difunctional monomers, and will be most evident when these monomers are present in equal amounts. The combination of crosslinking and an alternating structure is believed responsible for the slow release rate of the triorganotin species, which could explain the long-term biological activity of the present polymers. It will therefore be understood that equal concentrations of triorganotin compound and other difunctional comonomers are usually preferred, although monomer mixtures containing from 30 to 70 mole % of the triorganotin compound also yield useful products.

The present crosslinked, biologically active polymers can be applied to a variety of materials and other substrates, including fabrics, metal and plants, particularly food crops, in the form of compositions containing an inert diluent. The inert diluent can be a liquid hydrocarbon such as benzene, toluene, naphtha, mineral spirits or ligroin. Alternatively, the inert diluent can also be a liquid dispersant which is not a solvent for the polymer, e.g. water. Other suitable inert diluents include solid diluents and carriers such as talc, limestone or diatomaceous earth. Other preferred inert diluents include the non-film forming components of oil-based water-based paints. If desired, the biologically active polymer can replace part or all of the film-forming polymer in paints.

Where the biologically active polymer is employed in a composition containing an inert diluent, the biologically active polymer typically comprises from 0.01% to 80% by weight of the total composition. Preferably, it comprises from 0.2% to about 60% of the composition.

The particular composition employed and the amount of biologically active polymer contained therein are selected in accordance with the material to be treated and the organism against which protection is desired. According to certain preferred embodiments of this invention, the biologically active polymers are employed as the active ingredient of antifouling coating compositions, including paints. Typically antifouling paints contain a polymeric or resin base, including vinyl, acrylic, alkyd, epoxy, chlorinated rubber, urethane and polyester resin bases. They may also contain pigments such as cuprous oxide, iron oxide and titanium dioxide; thickeners such as bentonite; fillers such as talc, aluminum silicate and calcium silicate; and driers such as cobalt naphthenate and manganese naphthenate. These compositions also usually contain solvents or thinners typified by mineral spirits, naphtha, benzene, toluene and methyl ethyl ketone. When the biologically active polymers of this invention are employed in antifouling marine coating compositions, they replace part or all of the film-forming polymer and are typically employed in the amount of about 1–50%, based on the weight of the total composition.

A typical antifouling paint prepared in accordance with this invention has the following composition wherein all parts are parts by weight.

| | |
|---|---|
| Titanium dioxide | 19.4 |
| Aluminum silicate | 5.8 |
| Fibrous talc | 3.4 |
| High flash naphtha | 54.2 |
| Toluene | 18.2 |
| Crosslinked Tri-n-butyltin meth- | 15.3 |

-continued acrylate-methyl methacrylate copolymer.

In accordance with certain other preferred embodiments, the biologically active polymers of this invention can be used as the active ingredients of agricultural treatment compositions which are employed in the treatment of plants, seeds, tubers, and the like. They are particularly useful in this respect because of their markedly and unexpectedly reduced phytotoxicity. The polymers of triphenyltin compounds (i.e. those wherein $R^1$ is phenyl) possess particularly low phytotoxicity. Agricultural treating compositions can be prepared in the form of dusting powers or wettable powders. They typically contain adjuvants or carriers such as clay, diatomaceous earth, limestone, and talc. Dusting powders are usually applied as such, while wettable powders are dispersed in a liquid diluent, preferably water, before application. In accordance with this invention, the biologically active polymer typically constitutes from about 1 to about 60% by weight of the agricultural treatment composition. Where the composition is a wettable powder, the biologically active polymer is typically present in the amount of 10–60% and preferably 15–40% by weight of the composition. Wettable powders can be applied to plants by dispersing from 0.25 to about 5 pounds of wettable powder in 100 gallons of water. Such dispersions contain the biologically active polymer in a concentration of 0.005–0.25%, preferably 0.01–0.05% by weight. Plants are treated with the dispersion by spraying at the rate of 100–150 gallons of dispersion per acre.

A typical wettable powder formulated in accordance with this invention has the following composition, wherein all parts are parts by weight.

| Crosslinked triphenyltin methacrylate copolymer | 20.0 |
| Attapulgus clay[1] | 76.0 |
| Wetting agent[2] | 4.0 |

[1]Hydrous magnesium aluminum silicate.
[2]Contains 2.0 parts of lignin sulfonate and 2.0 parts ethylene oxide-nonyl phenol adduct (9 moles ethylene oxide per mole of phenol).

This wettable powder can be dispersed in water in the ratio of one pound of powder per 100 gallons of water and the resulting dispersion sprayed over 1 acre of plants.

Mildew and bacteria resistant paints containing the biologically active polymers can be employed wherever the growth of organisms is undesirable. For example, they can be used in hospitals, dairies, breweries and the like to control the growth of infectious organisms, or on exterior wooden surfaces to prevent dry rot or mildew growth. Mildew and bacteria resistant paints are either water-based paints (including those containing butadiene-styrene polymers, butadiene-acrylonitrile polymers and vinyl acetate polymers), or oil-based paints (including those containing alkyd polymers, natural varnishes and phenol-formaldehyde polymers). Such paints typically also contain pigments, thickeners, fillers, driers, solvents and thinners. Mildew and bacteria resistant paints formulated in accordance with this invention typically contain about 0.05–30% of biologically active polymer based on the weight of the total paint. Preferred mildew and bacteria resistant paints contain about 0.1–1.0% biologically active polymer.

A typical mildew and bacteria resistant paint formulated in accordance with this invention has the following composition wherein all parts are parts by weight.

| Titanium dioxide | 26.2 |
| Calcium silicate | 4.4 |
| Calcium carbonate | 19.5 |
| Magnesium silicate | 8.2 |
| Isophthalic acid-menhaden oil alkyd | 11.6 |
| Blown menhaden oil | 3.9 |
| Cobalt naphthenate drier | 1.1 |
| Manganese naphthenate drier | 0.4 |
| Crosslinked tri-n-butyltin methacrylate copolymer | 0.1 |
| Mineral spirits | 24.7 |

Another preferred biologically active composition based upon the novel biologically active polymers of this invention is an aerosol spray composition. Aerosol spray compositions formulated in accordance with this invention typically contain a solvent or diluent, a propellant, and as an active ingredient, the biologically active polymers of this invention.

A typical spray formulation contains about 10–30% by weight solvent, 69–89% by weight propellant and about 0.01–1.0% by weight biologically active polymer. A typical aerosol spray composition of this invention is as follows wherein all parts are parts by weight.

| Crosslinked tri-n-butyltin methacrylate copolymer | 0.1 |
| Toluene | 0.15 |
| Isopropanol | 15.0 |
| Propellant (dichlorodifluoromethane) | 84.75 |

Materials treated with any of the above compositions are rendered resistant to attack by bacteria, fungi, mildew, mold and marine organisms, for unexpectedly long period of use.

The following examples illustrate the present method and the improved polymers obtained thereby.

EXAMPLE 1

This example demonstrates the preparation of a preferred crosslinked triorganotin-containing polymer. A one liter capacity polymerization reactor equipped with a nitrogen inlet, water cooled condenser, thermometer, and mechanically driven stirrer was charged with 158 g. of tributyltin methacrylate, 49 g. of methyl methacrylate, 1.0 g. of 1,3-butanediol dimethacrylate, 0.2 liter of heptane and 0.9 g. of benzoyl peroxide (equivalent to 0.4%, based on total monomer weight). The contents of the reactor were heated at 80° C. for 18 hours to obtain a 95% conversion to polymer.

For purposes of comparison a second polymer was prepared using the foregoing procedure with 158 g. of tri-n-butyltin methacrylate, 49 g. methyl methacrylate and 0.9 g. benzoyl peroxide. No crosslinking agent was employed. Films prepared using this polymer were relatively soft and easily scratched. Films prepared using the crosslinked polymer were considerably harder and resistant to scratching.

The biological activity of triorganotin-containing polymers results from hydrolysis of the triorganotin moieties to the corresponding oxide or hydroxide, which is believed to be the active species. The rate at which this hydrolysis occurs will therefore determine the concentration of active species at any given time as well as the duration of biological activity, since once the active species is formed it can readily be removed from the substrate. This is paticularly true when the substrate is immersed in an aqueous medium which occurs if the polymers are incorporated into antifouling coatings. It would therefore be desirable to be able to control the rate of hydrolysis by controlling the structure of the polymer. The present polymers achieve this goal by a judicious selection of crosslinking agent concentration and the proper liquid polymerization medium.

EXAMPLE 2

This example illustrates the use of a preferred biologically active polymer as an antifouling agent. Fiberglass discs with a 2.5 inch radius were coated with films prepared using a 40% by weight solution in heptane of the crosslinked and non-crosslinked polymers disclosed in Example 1. The two test discs together with a number of untreated discs were immersed below tide level in the clean at Key Biscayne, Florida. The discs were immersed so as to test both plant and animal fouling resistance. After four weeks immersion, the untreated discs were completely fouled. Both treated discs were free of fouling organisms. The disc coated with non-crosslinked polymer was free of fouling for a distance of one inch (2.5 cm.) beyond the circumference of the test area. The disc coated with crosslinked polymer was free of fouling only within the test area. These results show that the crosslinked polymer swelled less than the non-crosslinked polymer, resulting in a lower hydrolytic release rate for the active organotin species.

EXAMPLE 3

This example compares the biological activity of crosslinked and non-crosslinked polymers against bacteria and fungi. In these tests a nutrient agar medium was melted and inoculated with the desired organism. The seeder agar was then placed in a petri dish and a 6mm. well cut from the center of the agar. The material to be tested was placed in the well. The dishes were then refrigerated at 5° C. for 24 hours, after which they were incubated either at 37° C. for 24 hours for testing against bacteria or at 30° C. for 5 days for testing against fungi.

Following the incubation period the dishes were examined and ratings of the activity of the test materials determined by measuring the distance from the edge of the well which remains free of test organism growth. The distance, in millimeters, of the zone of complete inhibition is an indication of the activity of the test material.

Table 1 summarizes the test materials, test organisms, and activity of crosslinked and non-crosslinked polymers.

Table 1

| Test Material | Bacteria | | Fungi | |
|---|---|---|---|---|
| | Staphylococcus aureus | Pseudomonas aeruginosa | Aspergillus niger | Penicillium fumiculosum |
| Non-crosslinked polymer (control) | 10 | 4 | 7 | 7 |
| Crosslinked polymer | 6 | 3 | 5 | 5 |

The data demonstrate that the biologically active polymers are satisfactory fungicides and bactericides. The tougher film formed by the crosslinked polymer had a smaller zone of inhibition than the non-crosslinked polymer, which is indicative of a slower hydrolysis rate for the triorganotiin moiety.

What is claimed is:

1. A biologically active copolymer obtained by reacting in the presence of a free radical polymerization initiator and a liquid hydrocarbon medium at least one solubilized triorganotin compound of the general formula

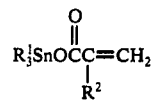

with at least one solubilized copolymerizable monomer of the general formula

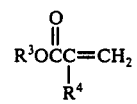

and from 0.01 to 10%, based on total monomer weight, of a crosslinking agent selected from the group consisting of divinyl benzene, compounds of the formulae

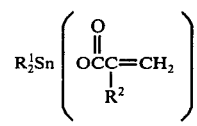

and

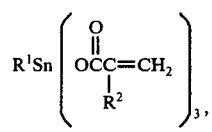

esters of acrylic or metharylic acid with polyfunctional alcohols and phenols, wherein said esters contain from 2 to 4 residues of said acid, and wherein each $R^1$ is individually selected from the group consisting of alkyl radicals containing from 1 to 8 carbon atoms, cycloalkyl and aryl radicals, $R^2$ and $R^4$ are individually selected from hydrogen and methyl radicals and $R^3$ represents an alkyl radical containing from 1 to 18 carbon atoms, a cyclohexyl or a phenyl radical.

2. A biologically active copolymer as set forth in claim 1 wherein the polymerization medium consists essentially of at least one liquid aliphatic or cycloaliphatic hydrocarbon containing from 5 to 16 carbon atoms.

3. A biologically active copolymer as set forth in claim 2 wherein said medium consists essentially of at least one aliphatic hydrocarbon containing from 7 to 14 carbon atoms.

4. A biologically active copolymer as set forth in claim 3 wherein said medium contains from 50 to 100% by volume of said aliphatic hydrocarbon any remaining portion of said medium being a liquid aromatic hydrocarbon.

5. A biologically active polymer as set forth in claim 4 wherein said aliphatic hydrocarbon is heptane or a mixture of aliphatic hydrocarbons containing heptane as a major constituent and said liquid aromatic hydrocarbon is xylene.

6. A biologically active copolymer as set forth in claim 1 wherein said triogranotin compound constitutes from 10 to 90 mole % of the total monomers.

7. A biologically active copolymer as set forth in claim 6 wherein said triorganotin compound constitutes from 30 to 70 mole % of the total monomers.

8. A biologically active copolymer as set forth in claim 1 wherein the concentration of monomers is from 1.5 to 5 moles per liter of reaction mixture.

9. A biologically active copolymer as set forth in claim 8 wherein said concentration is greater than 2 moles per liter.

10. A biologically active copolymer as set forth in claim 1 wherein the reaction is conducted at a temperature from 70° to 85° C.

11. A biologically active copolymer as set forth in claim 1 wherein the concentration of polymerization initiator is from 0.001 to 0.01 mole %, based on total monomers.

12. A biologically active copolymer as set forth in claim 1 wherein said crosslinking agent is an ester of acrylic or methacrylic acid and a difunctional alcohol.

13. A biologically active copolymer as set forth in claim 12 wherein said difunctional alcohol is 1,3-butanediol.

14. A biologically active polymer as set forth in claim 1 wherein the concentration of said crosslinking agent is from 0.1 to 5%, based on total monomer weight.

* * * * *

UNITED STATES PATENT OFFICE
CERTIFICATE OF CORRECTION

Patent No. 4,121,034    Dated October 17, 1978

Inventor(s) JOHN R. BEDNARSKI ET AL.

It is certified that error appears in the above-identified patent and that said Letters Patent are hereby corrected as shown below:

Claim 1, line 13 - Delete the formula

"$R_2^1 Sn \begin{bmatrix} O \\ \| \\ OCC=CH_2 \\ \phantom{O}\phantom{|}R^2 \end{bmatrix}$" and substitute therefor --$R_2^1 Sn \begin{bmatrix} O \\ \| \\ OCC=CH_2 \\ \phantom{O}\phantom{|}R^2 \end{bmatrix}_2$ --.

Abstract of the Disclosure, line 3 - Delete "($R_3 SN-$)" and substitute therefor --($R_3 Sn-$)--.

Column 7, line 37 - Delete "seeder" and substitute therefor --seeded--.

Signed and Sealed this

Sixteenth Day of January 1979

[SEAL]

Attest:

RUTH C. MASON
Attesting Officer

DONALD W. BANNER
Commissioner of Patents and Trademarks